(12) United States Patent
Agnihotri et al.

(10) Patent No.: US 12,369,906 B1
(45) Date of Patent: Jul. 29, 2025

(54) SUTURE FASTENER AND DELIVERY DEVICE

(71) Applicant: cLoc Medical Inc., Maple Grove, MN (US)

(72) Inventors: Aashiish Agnihotri, Maple Grove, MN (US); Damian Jelich, Cottage Grove, MN (US); Jeffrey Sandstrom, Scandia, MN (US); Trevor Laughlin, Minneapolis, MN (US)

(73) Assignee: cLoc Medical Inc., Maple Grove, MN (US)

( * ) Notice: Subject to any disclaimer, the term of this patent is extended or adjusted under 35 U.S.C. 154(b) by 0 days.

(21) Appl. No.: 19/035,170

(22) Filed: Jan. 23, 2025

Related U.S. Application Data (60) Provisional application No. 63/742,242, filed on Jan. 6, 2025.

(51) Int. Cl.
*A61B 17/04* (2006.01)

(52) U.S. Cl.
CPC ...... *A61B 17/0469* (2013.01); *A61B 17/0483* (2013.01); *A61B 2017/0479* (2013.01)

(58) Field of Classification Search
CPC ............ A61B 17/0469; A61B 17/0483; A61B 2017/0479; A61B 2017/0488; A61B 2017/06014
USPC .......................................................... 606/1
See application file for complete search history.

(56) References Cited

U.S. PATENT DOCUMENTS

| | | | |
|---|---|---|---|
| 7,235,086 B2 | 6/2007 | Sauer et al. | |
| 7,785,348 B2 | 8/2010 | Kuhns et al. | |
| 8,075,573 B2 * | 12/2011 | Gambale | A61B 17/0469 606/145 |
| 8,100,939 B2 * | 1/2012 | Peterson | A61B 17/064 606/213 |
| 8,197,497 B2 | 6/2012 | Nobles et al. | |
| 8,613,756 B2 | 12/2013 | Lizardi et al. | |
| 9,089,325 B2 | 7/2015 | Mitelberg et al. | |
| 9,592,048 B2 | 3/2017 | Moehle et al. | |
| 9,848,984 B2 | 12/2017 | Conklin et al. | |
| 10,624,630 B2 | 4/2020 | Deville et al. | |
| 11,395,650 B2 | 7/2022 | Miraki | |
| 11,576,667 B2 | 2/2023 | Conklin et al. | |
| 2003/0167062 A1 * | 9/2003 | Gambale | A61B 17/0487 606/148 |
| 2007/0080188 A1 * | 4/2007 | Spence | A61F 2/2445 623/2.11 |

(Continued)

*Primary Examiner* — Ahmed M Farah
(74) *Attorney, Agent, or Firm* — Best & Flanagan LLP (57) ABSTRACT

A suture fastener delivery device includes a handle, a fastener delivery end comprising a suture fastener and crimping jaws, and a shaft extending between the handle and the fastener delivery end. The shaft comprises a rail, a plurality of reserve suture fasteners, a side suture slot positioned on a side of the shaft to allow the suture ends to exit the delivery device, and a suture cutting blade adjacent to the rail. The suture fastener delivery device can capture a suture within a side slot of the suture device, and upon activation of a trigger on the handle, crimp and bend the suture fastener to secure the fastener, and cut the excess suture ends via the cutting blade. A slider on the handle can then be used to reload a reserve suture fastener, such that additional fasteners can be deployed without removal of the delivery device from the surgical site.

18 Claims, 8 Drawing Sheets

(56) References Cited

U.S. PATENT DOCUMENTS

| | | | |
|---|---|---|---|
| 2009/0030434 A1* | 1/2009 | Paz | A61B 17/064 606/1 |
| 2013/0158600 A1* | 6/2013 | Conklin | A61B 17/0401 606/232 |
| 2016/0310129 A1* | 10/2016 | Hoeppner | A61B 17/0483 |
| 2018/0049875 A1* | 2/2018 | Iflah | A61F 2/2412 |
| 2023/0149005 A1* | 5/2023 | Agnihotri | A61B 17/0401 606/153 |
| 2024/0081800 A1* | 3/2024 | Iamberger | A61B 17/0469 |

* cited by examiner

SUTURE FASTENER AND DELIVERY DEVICE

BACKGROUND OF THE INVENTION

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Surgical sutures can be secured via hand tied knots, instrument tied knots, or by deforming a malleable material around strands of the suture, thereby securing it. Instruments which allow deployment of such malleable material must be precise and intuitive for a clinician to use in order to ensure that the sutures are appropriately secured. Such instruments can present challenges to a clinician such as difficulties in making appropriate contact with sutures to be secured, and continually moving out of the sterile surgical field to obtain new suture fasteners to secure additional sutures. Therefore, improvements in instruments relating to deployment of suture fasteners, and suture fasteners themselves are desirable.

BRIEF SUMMARY OF THE INVENTION

The following presents a simplified summary of one or more embodiments of the present disclosure in order to provide a basic understanding of such embodiments. This summary is not an extensive overview of all contemplated embodiments, and is intended to neither identify key or critical elements of all embodiments, nor delineate the scope of any or all embodiments.

In one or more embodiments, a suture fastener delivery device comprises a controller positioned on a proximal end of the suture fastener delivery device, the controller comprising at least one control element, a fastener delivery end positioned on a distal end of the suture fastener delivery device, the fastener delivery end comprising a suture fastener configured to be deployed to secure a suture and crimping jaws positioned about an outer surface of the suture fastener, and a shaft extending between the controller and the fastener delivery end from the proximal end to the distal end of the suture fastener delivery device. The shaft comprises a rail extending along an interior length of the shaft, a plurality of reserve suture fasteners mounted along the rail, a side suture slot positioned about a side of the shaft, the side suture slot configured to allow the suture to exit the suture fastener delivery device, and a suture cutting blade, the suture cutting blade positioned adjacent to the rail within the shaft.

In some embodiments, the suture fastener comprises a side opening and wherein the suture fastener is configured to receive the suture though the side opening.

In at least one embodiment, the fastener delivery end further comprises a suture trap, configured to receive the suture and pass the suture into the suture fastener. The suture trap comprises a one-way channel allowing sutures to enter the suture trap from a top side of the one-way channel.

In at least one embodiment, the at least one control element comprises a trigger and a slider. The crimping jaws are configured to crimp the suture fastener around the suture in response to activation of the at least one control element, thereby securing the suture. The suture cutting blade is configured to move in a direction substantially parallel to the rail to cut a trailing end of the suture in response to activation of the at least one control element. The suture fastener is bent in the first direction in response to activation of the at least one control element.

In at least one embodiment, the plurality of reserve suture fasteners are positioned as a spring-loaded stack. The shaft further comprises a stack gate configured to halt the spring-loaded stack of the reserve suture fasteners from contacting the fastener delivery end. The shaft further comprises a pusher element, and wherein in response to activation of the at least one control element, the pusher element pushes a most distal suture fastener of the reserve suture fasteners over the stack gate and into contact with the fastener delivery end. In at least one embodiment, the pusher element comprises two tines.

In at least one embodiment, the suture fastener has a C-shaped cross-section.

In at least one embodiment, the suture fastener is integrally formed as a singular piece.

In at least one embodiment, the suture fastener comprises a collar on the suture fastener, the collar configured to rest upon tissue when the suture fastener is deployed.

In at least one embodiment, the side suture slot is a curved three-dimensional feature allowing one directional passage of sutures.

In at least one embodiment, the suture fastener comprises two elongated elements and a locking mechanism. In at least one embodiment, the suture fastener comprises an open loop element and a locking mechanism, the open loop element being made of nitinol.

In some embodiments, a method for installing a suture fastener within a surgical field via a suture fastener delivery device, wherein the suture fastener delivery device comprises a controller positioned on a proximal end comprising a first control element and a second control element, a fastener delivery end positioned on a distal end comprising a suture fastener and crimping jaws positioned about an outer surface of the suture fastener, and a shaft extending between the controller and the fastener delivery end, the shaft comprising a rail extending along the interior length of the shaft, a plurality of reserve suture fasteners mounted along the rails, a side suture slot positioned about a side of the shaft, and a suture cutting blade positioned adjacent to the rail within the shaft, includes: positioning the suture fastener delivery device such that a side opening of the suture fastener is adjacent to a suture, capturing the suture within the suture fastener such that the suture rests within a body of the suture fastener, and exits through the side suture slot, activating the first control element, deforming the suture fastener via crimping jaws in response to activation of the first control element, cutting a trailing end of the suture via the suture cutting blade in response to activation of the first control element, bending the suture in a predetermined direction via the crimping jaws in response to activation of the first control element, activating a second control element, and pushing a reserve suture fastener over a stack gate via a pushing mechanism such that the reserve suture fastener is in contact with the fastener delivery end and in a deployment position in response to activation of the second control element.

In at least one embodiment, the reserve suture fastener is placed in the deployment position while the suture fastener delivery device remains in the surgical field.

While multiple embodiments are disclosed, still other embodiments of the present disclosure will become apparent to those skilled in the art from the following detailed description, which shows and describes illustrative embodiments of the invention. As will be realized, the various embodiments of the present disclosure are capable of modifications in various obvious aspects, all without departing from the spirit and scope of the present disclosure. Accordingly, the drawings and detailed description are to be regarded as illustrative in nature and not restrictive.

BRIEF DESCRIPTION OF THE DRAWINGS

While the specification concludes with claims particularly pointing out and distinctly claiming the subject matter that is regarded as forming the various embodiments of the present disclosure, it is believed that the disclosure will be better understood from the following description taken in conjunction with the accompanying Figures, in which:

DETAILED DESCRIPTION

In the following detailed description, numerous specific details are set forth in order to provide a thorough understanding of some embodiments. However, it will be understood by persons of ordinary skill in the art that some embodiments may be practiced without these specific details. In other instances, well-known methods, procedures, and/or components have not been described in detail so as not to obscure the discussion.

The present disclosure describes a novel and advantageous suture fastener delivery device as well as a novel and advantageous suture fastener. The suture fastener delivery device includes a handle, a robotic control arm, or a similar device on a proximal end (i.e., proximal to the user) a fastener delivery mechanism on the distal end (i.e., distal from the user), and a shaft extending between the proximal end and the distal end. The handle comprises one or more control elements for using the suture fastener delivery device. The shaft comprises a rail having a spring-loaded stack of reserve suture fasteners mounted on the rail. The shaft also includes a stop mechanism preventing the reserve suture fasteners from contacting the fastener delivery mechanism, a pusher element for pushing the next reserve suture fastener over the stop mechanism and to the fastener delivery mechanism, a side suture slot for receiving sutures, and a suture cutting blade for cutting sutures once secured. The fastener delivery mechanism includes a suture fastener to be deployed, and crimping jaws positioned about the suture fastener.

In operation, the suture fastener delivery device can be maneuvered such that sutures rest within the suture fastener and the trailing ends of the suture extend through the side slot in the shaft of the delivery device. Upon activation of the control mechanism, the suture fastener delivery device can activate the crimping jaws to deform the suture fastener, deploy the cutting mechanism to cut the excess strands of the suture, and bend the deployed suture fastener in a predetermined direction. Additionally, via the control mechanism, a new suture fastener can be pushed from the reserve suture fastener stack via the pusher, such that the new suture fastener is ready for deployment. This allows for the suture fastener delivery device to apply multiple suture fasteners (e.g., 10, 20, or more than 20 suture fasteners) without removing the suture fastener delivery device from the surgical field, thereby reducing the risk of infection.

Figure 1:
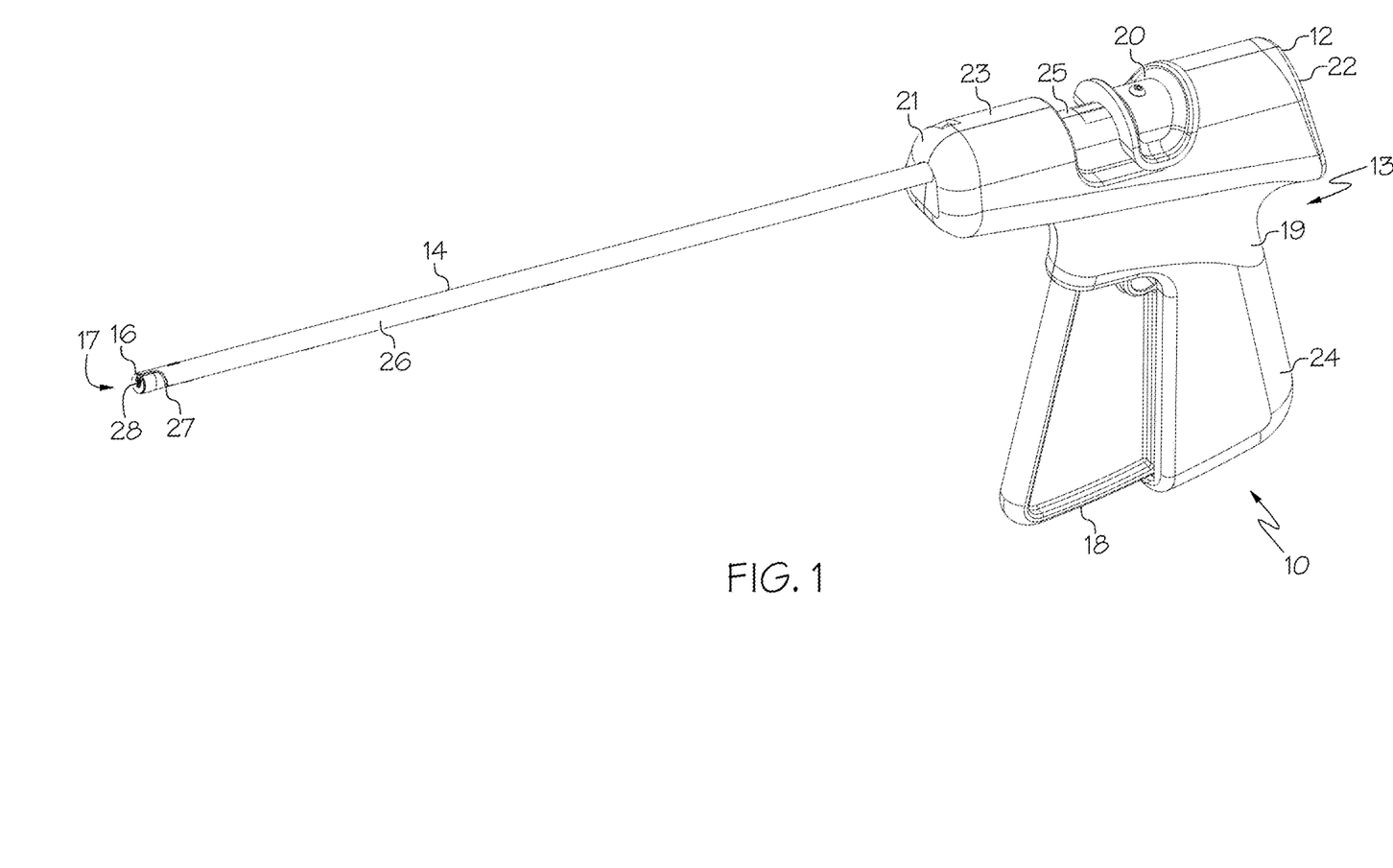
FIG. 1 is a perspective view of a suture fastener and delivery device.
Figure 2A:
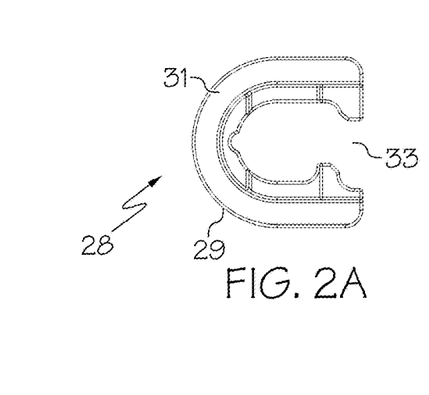
FIG. 2A is a front view of a suture fastener.
Figure 2B:
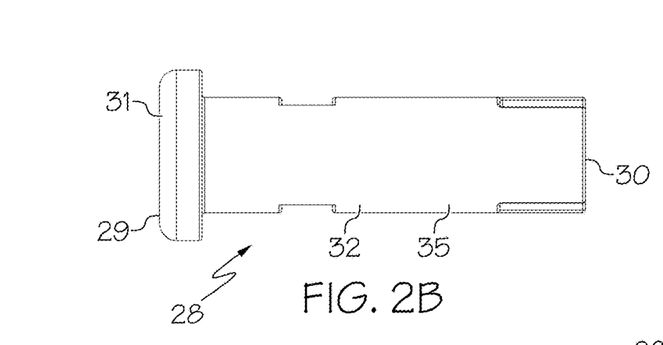
FIG. 2B is a side view of the suture fastener.
Figure 2C:
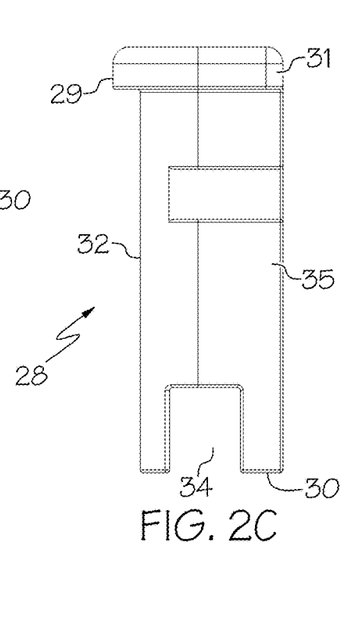
FIG. 2C is a bottom view of the suture fastener.
Figure 2D:
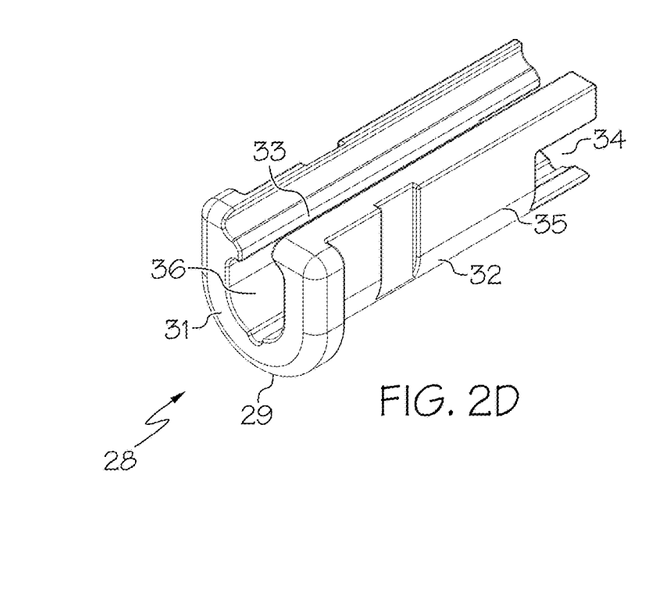
FIG. 2D is a perspective view of the suture fastener.
Figure 2E:
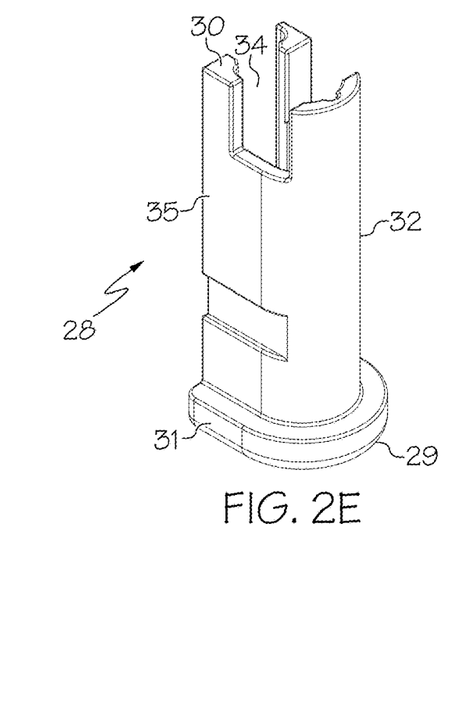
FIG. 2E is an additional perspective view of the suture fastener.

FIGS. 1-6 depict a suture fastener delivery system, including a suture fastener delivery device and a suture fastener, according to one or more embodiments of the invention described herein. FIG. 1 depicts a perspective view of one embodiment of suture fastener delivery device 10. Suture fastener delivery device 10 includes a controller at proximal end 13. The controller can be handle 12, a robotic control arm, or a similar device. Suture fastener delivery device 10 further includes fastener delivery end 16 at distal end 17, and shaft 14 extending between handle 12, or more generally, the controller, and fastener delivery end 16. Handle 12 includes a first control mechanism such as trigger 18, a second control mechanism such as slider 20, and body 19. While trigger 18 is depicted as the first control mechanism and slider 20 is depicted as the second control mechanism in FIG. 1, various alternative control mechanisms (e.g., push buttons, switches, touch activated buttons, etc.) can be used.

In some embodiments, as shown in FIG. 1, body 19 has a front end 21, a rear end 22, a barrel portion 23, and a gripping portion 24. Shaft 14 is connected to barrel portion 23 of body 19 at front end 21. Gripping portion 24 of handle 12 can, for example, be a downward protruding element from barrel portion 23 designed to allow a user to grip handle 12. In some embodiments, gripping portion 24 of handle 12 includes a rubber, silicone, or other polymers for enhancing the grip of a user about handle 12.

In the embodiment shown in FIG. 1, trigger 18 is disposed relative to the gripping portion 24 of handle 12. In at least the embodiment shown, trigger 18 is mechanically connected to the body 19 and positioned below the slider 20 and/or below barrel portion 23. Gripping portion 24 of handle 12 can include a cavity for receiving at least a portion of trigger 18 when trigger 18 is actuated. In other embodiments, trigger 18, or an alternative first control mechanism, can be positioned differently upon handle 12. In one such embodiment, trigger 18 can be positioned on rear end 22 of handle 12, which could be activatable by the thumb of a user. In other embodiments, trigger 18 can be positioned on a portion of handle 12 other than gripping portion 24. In such an example, trigger 18 can be positioned on an underside of barrel portion 23 of handle 12, and in some embodiments, trigger 18 is activatable by the finger of user. It is understood that the trigger 18, and more generally the first control mechanism, can be positioned on any part of handle 12.

In embodiment shown in FIG. 1, slider 20 is positioned on the barrel portion 23 of handle 12. Barrel portion 23 of handle 12 can include cavity 25 which houses slider 20 and provides a channel for slider 20 to be pushed forward towards front end 21. In alternative embodiments, cavity 25 and slider 20 can be oriented such that slider 20 is activated by pulling slider 20 towards rear end 22. In still other embodiments, slider 20, and more generally the second control mechanism, can be positioned alternatively about handle 12. In one such embodiment, slider 20 can be positioned on either side of handle 12.

The first control mechanism (e.g., trigger 18) is operationally connected to the fastener delivery end 16 via the shaft 14 and the second control mechanism (e.g., slider 20) is operationally connected to at least shaft 14. Shaft 14 includes sidewall 26, side suture slot 27 disposed within sidewall 26, an inner channel defined by sidewall 26, and a stack of reserve fasteners 52 disposed within the inner channel (shown best in FIG. 4). Side suture slot 27 is positioned on shaft 14 near distal end 17. Side suture slot 27, in at least the embodiment shown, is curved around at least a portion of shaft 14, and extends from fastener delivery end 16 to a side of shaft 14. Fastener delivery end 16 includes suture fastener 28, which is in position for deployment.

In operation, the suture fastener delivery device 10 can be maneuvered to capture at least a portion of an implanted suture within suture fastener 28. The suture is captured such that trailing ends of the suture extend through side suture slot 27. Upon activation of the first control mechanism (e.g., trigger 18), suture fastener delivery device 10 can activate crimping jaws 60 (shown best in FIG. 6) within fastener delivery end 16 to deform suture fastener 28 thereby securing the suture within the deformed suture fastener 28. In some embodiments, the crimping jaws are shaped such that the deformed suture fastener 28 is in a bent shape. Additionally, in some embodiments, upon activation of trigger 18, suture fastener delivery device 10 can deploy a cutting mechanism (shown best in FIG. 6) within shaft 14 to cut the trailing ends of the suture extending through side suture slot 27. In some embodiments, the deformation of the suture and the cutting of the suture ends occur in response to a single activation of the first control mechanism. In other embodiments, suture fastener 28 is deformed in response to a first pressure exerted upon trigger 18 and the suture is cutting with the cutting mechanism in response to a second pressure exerted upon trigger 18. Further, upon activation of the second control mechanism, a new suture fastener can be pushed from reserve suture fasteners 52 (shown best in FIGS. 4-6) within shaft 14, such that the new suture fastener is ready for deployment. Additional description of the features of suture fastener 28 will be disclosed in the description of FIG. 2. Additional description of the internal features of shaft 14 will be disclosed in the description of FIGS. 3-6.

Suture fastener delivery device 10 provides several advantages. Suture fastener delivery device 10 allows for securing an implanted suture via suture fastener 28. Further, within suture fastener delivery device 10, a single control mechanism accomplishes multiple functions. As described, activation of the first control mechanism results in crimping and bending of suture fastener 28 in a predetermined direction, as well as cutting of the suture via a cutter within shaft 14. Further, after deployment of suture fastener 28, a reserve suture fastener can take the place of the deployed suture fastener via activation of the second control mechanism, thereby preparing suture fastener delivery device 10 to deploy another suture fastener without having to remove suture fastener delivery device 10 from the surgical environment to reload the device. Thus, suture fastener delivery device can, for example, deploy 10, 20 or more than 20 suture fasteners thereby saving time in procedures where multiple sutures must be fastened in close proximity such as mitral/tricuspid valve annuloplasty, or surgical aortic valve replacements.

FIGS. 2A-2E respectively depict a front view, a side view, a bottom view, a perspective view, and an additional perspective view of suture fastener 28. Suture fastener 28 can comprise one or more of the following materials: titanium or other ductile metals, polymers, and/or resorbable polymers. It is understood that additional materials suitable for suture fastening can be used in combination with, or instead of, the listed materials. Suture fastener 28 includes first end 29, second end 30, collar 31, body 32, slot 33, and rear openings 34. Body 32 includes outer surface 35 and inner surface 36. Collar 31 and body 32 are integrally formed such that suture fastener 28 is a monolithic, singular piece. Collar 31 is positioned at first end 29. Body 32 extends from collar 31 to second end 30. Slot 33 defines a cavity in a side of body 32 and collar 31, thereby providing suture fastener 28 with a C-shaped cross section. In some embodiments, collar 31 has a larger cross-sectional area than body 32 due to the overhanging shape of collar 31. Rear openings 34 define cavities on a top side and a bottom side of body 32.

In operation, suture fastener 28 is positioned at fastener delivery end 16 of suture fastener delivery device 10 for deployment. In some embodiments, the suture can enter body 32 through slot 33. At least a portion of the trailing ends of the suture can extend out of suture fastener delivery device 10 through shaft 14 via side suture slot 27, as shown in FIG. 1. Upon activation of the first control mechanism, crimping jaws (best depicted in FIG. 6) positioned about outer surface 35 can deform suture fastener 28 such that the sutures are secured within slot 33. Suture fastener 28 can also be bent in a predetermined direction via activation of the first control mechanism due to the shape and orientation of crimping jaws 60. Additional description regarding the bending of suture fastener 28 via crimping jaws 60 will be disclosed in the description of FIGS. 6-7C. Upon activation of the second control mechanism, pusher element 54 can push a suture from reserve suture fasteners 52 into position at fastener delivery end 16. In doing so, pusher element 54 can engage with a suture fastener of reserve suture fasteners 52 via rear openings 34 and push the suture fastener of reserve suture fasteners over stack gate 54 and hence in position for deployment. Additional description of the function of pusher element 54 will be disclosed in the description of FIGS. 4-6

Suture fastener 28 provides several advantages. Suture fastener 28 is integrally formed, relieving the necessity for multiple parts to form a suture fastener. Further, suture fastener 28 includes a C-shaped cross section, allowing sutures to received within cavity 31 and hence to be more easily received within an inner portion of body 32. Additionally, the configuration of collar 31 allows for suture fastener 28 to be securely positioned at fastener delivery end 16 of suture fastener delivery device 10.

Figure 3:
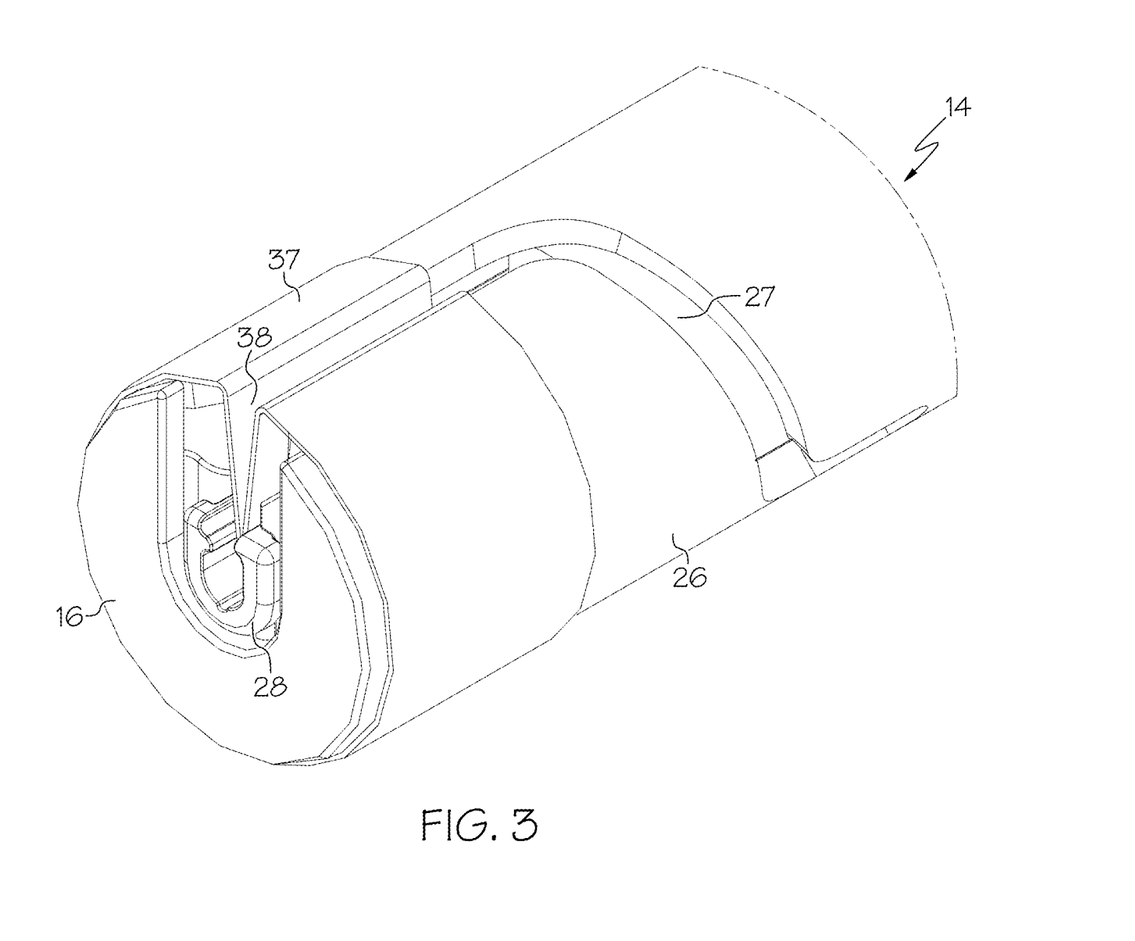
FIG. 3 is a perspective view of a distal end of the suture fastener delivery device.

FIG. 3 depicts the distal end of suture fastener delivery device 10, including shaft 14 and fastener delivery end 16. Shaft 14 includes side suture slot 27 extending within the sidewall 26 towards fastener delivery end 16. Fastener delivery end 16 includes suture fastener 28, and suture trap 37. Suture trap 37 includes channel 38. Suture trap 37 is positioned such that channel 38 axially extends from the end of fastener delivery end 16 to side suture slot 27. Channel 38 extends radially towards slot 33 of suture fastener 28.

Channel 38 narrows as channel 38 radially approaches slot 33. A bottom side of channel 38 is in communication with slot 33, thereby allowing sutures received within suture trap 37 to be directed through slot 33. A top side of channel 38 is in communication with side suture slot 27, thereby making the cavity from side suture slot 27 continuous to fastener delivery end 16.

In operation, a suture can be received in suture fastener 28 via suture trap 37 and at least a portion of the trailing ends of the suture can extend out of suture fastener delivery device 10 through shaft 14 via side suture slot 27. In one example, an operator of suture fastener delivery device 10 positions delivery device 10 such that a suture is adjacent to channel 38 of suture trap 37. Thereafter, the operator can move delivery device 10 to capture the suture, for example by a lateral movement of delivery device 10, resulting in the suture travelling down channel 38 and hence into suture fastener 28. The operator can use a wrist flick motion, or other such motion, to ensure suture fastener 28 is captured along the entire length of suture slot 27, and at least a portion of the trailing ends of the suture extend through side suture slot 27. In some embodiments, channel 38 of suture trap 37 is a one-way channel which comprises a structure allowing sutures to go from the top side of channel 38 to the bottom side of channel 38 and into suture fastener 28, but restricts sutures from going in the opposite direction from the bottom side of channel 38 to the top side of channel 38. In some embodiments, suture trap 37 extends along the length of suture slot 27. In such an embodiment, suture trap 37 can be made from, in one example, a soft polymer.

Suture trap 37 provides the advantage of being able to secure a suture within suture fastener 28 via a simple motion by the operator of delivery device 10. Further, the layout of channel 38 as being adjacent to side suture slot 27, and the curvature of side suture slot 27 about shaft 14 allows for the trailing ends of the suture extending through side suture slot 27 to be removed via a cutting blade.

Figure 4:
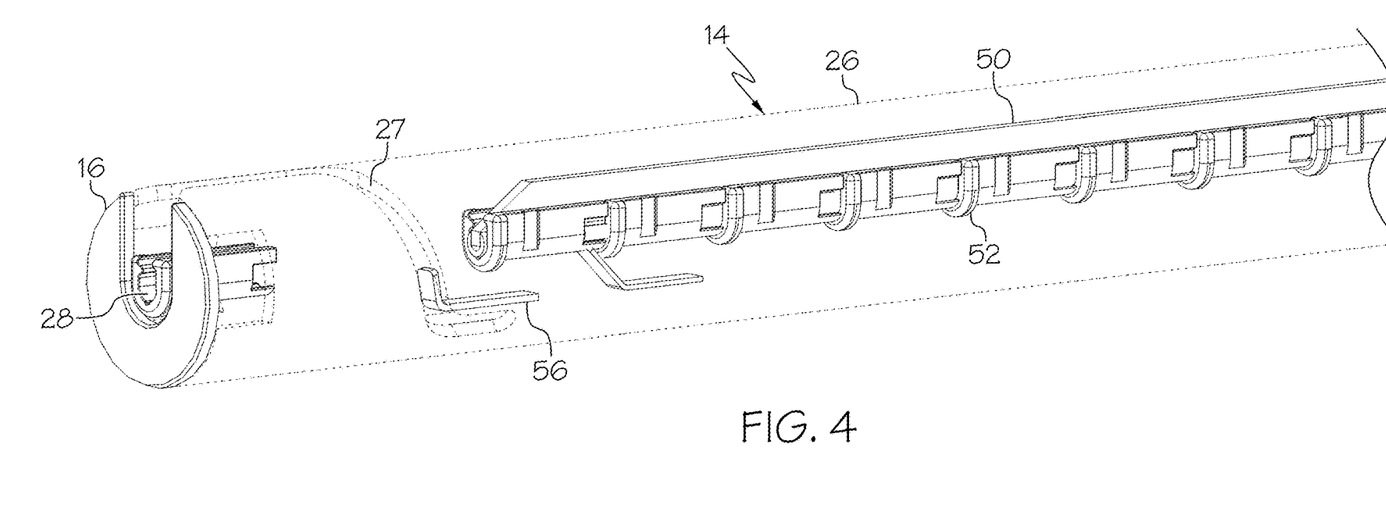
FIG. 4 is a perspective view of the internals of a shaft of the suture fastener delivery device.
Figure 5:
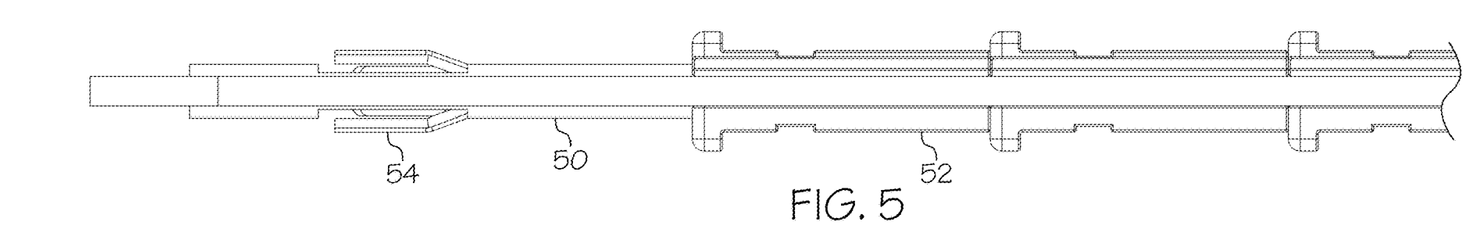
FIG. 5 is a side cross-sectional view of the shaft of the suture fastener delivery device including a pusher element.
Figure 6:
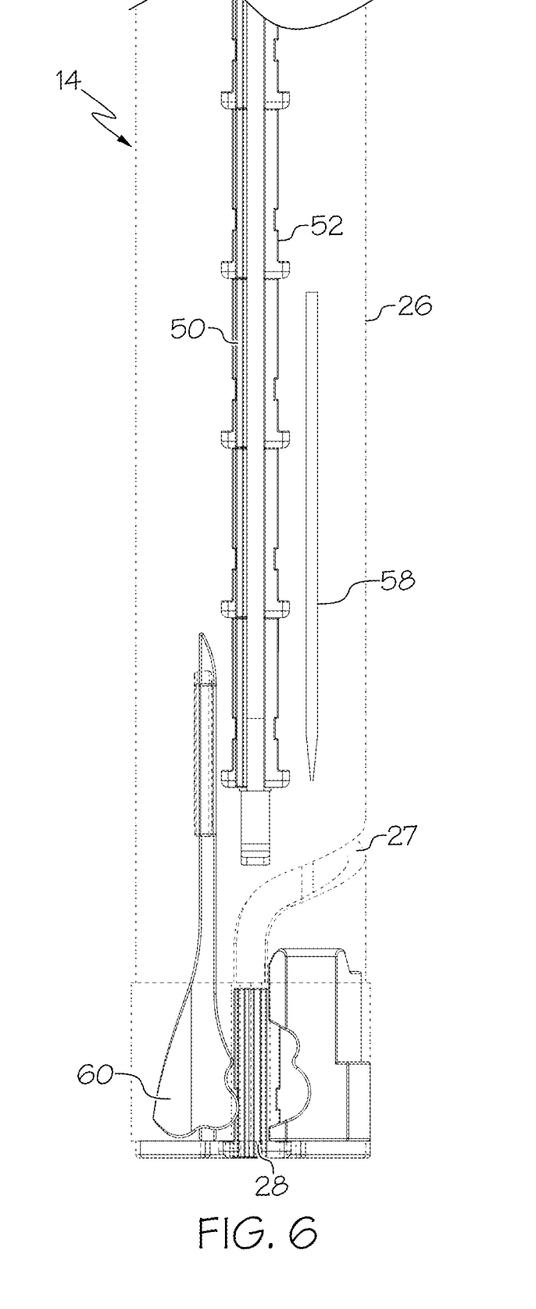
FIG. 6 is a top view of the internals of the shaft and the distal end of the suture fastener delivery device.

FIG. 4 depicts the internals of shaft 14 of suture fastener delivery device 10. FIG. 5 depicts a side cross-sectional view of shaft 14 of suture fastener delivery device 10 including pusher element 54. FIG. 6 is a top view of the internals of shaft 14 and fastener delivery end 16 of suture fastener delivery device 10. FIGS. 4-6 will be discussed together.

Shaft 14 includes rail 50, reserve suture fasteners 52, pusher element 54, side suture slot 27, stack gate 56, and suture cutting blade 58. Rail 50 extends along the interior of shaft 14. Reserve suture fasteners 52 are positioned as a stack and are mounted along rail 50. Reserve suture fasteners 52 are spring loaded. Stack gate 56 is positioned at a distal end of shaft 14 and stack gate 56 is in contact with the most distal suture fastener of reserve suture fasteners 52. Pusher element 54 is positioned on rail 50. Suture cutting blade 58 is positioned adjacent to rail 50 and adjacent to side suture slot 27 in the interior of shaft 14. Fastener delivery end 16 includes crimping jaws 60, and suture fastener 28. Crimping jaws 60 positioned on opposite sides of outer surface 35.

In operation, as described above, sutures are received within suture fastener 28 and exit suture fastener delivery device 10 via side suture slot 27. Upon activation of the first control mechanism (e.g., trigger 18), crimping jaws 60 enclose to deform suture fastener 28 and secure the suture. In some embodiments, crimping jaws 60 are in an anvil and hammer configuration, wherein hammer side of crimping jaws 60 is pushed downwards towards the anvil side. The anvil side can have a shaped indent, as depicted in FIG. 6, thereby shaping suture fastener 28 into a bent configuration. The imprint or orientation of crimping jaws 60 can be modified to change the direction of bending of suture fastener 28 when deformed. In other embodiments, crimping jaws 60 can comprise two moveable jaws which move towards each other in order to deform suture fastener 28.

Further, upon activation of the first control mechanism, suture cutting blade 58 is moved in a direction substantially parallel to rail 50 towards fastener delivery end 16. In doing so, suture cutting blade 58 cuts the suture ends extending from suture fastener 28 and through side suture slot 27. In some embodiments, suture cutting blade 58 cuts the suture ends simultaneous to the crimping of suture fastener 28. In other embodiments, suture cutting blade 58 cuts the suture ends after the crimping of suture fastener 28. In still other embodiments, the first control mechanism crimps suture fastener 28 in response to a first pressure being applied to the first control mechanism, and cuts the suture ends via suture cutting blade 58 in response to a second pressure being applied to the first control mechanism.

After suture fastener 28 is deployed, the most distal suture fastener within reserve suture fasteners 52 can replace suture fastener 28. As described, reserve suture fasteners 52 are spring loaded and coupled to rail 50. Stack gate 56 prevents reserve suture fasteners 52 from advancing past rail 50 and into fastener delivery end 16, between crimping jaws 60. Pusher element 54 can include two tines, the two tines being made from flexible material. Each of the two tines of pusher element 54 can be disposed about outer surface 35 of the most distal suture fastener within reserve suture fasteners 52, each of the two tines engaging with outer surface 35 via rear openings 34 of the suture fastener. Upon activation of the second control mechanism (e.g., slider 20), pusher element 54 can, via the two tines positioned about outer surface 35, push the most distal suture fastener of reserve suture fasteners 52 such that stack gate 56 is flexed out of its original and the suture fastener is pushed over the stack gate. Upon the suture fastener passing over stack gate 56, stack gate 56 can thereafter return to its original position, thereby restricting the remainder of reserve suture fasteners 52 from advancing to fastener delivery end 16. The suture fastener pushed by pusher element 54 is positioned within fastener delivery end 16 and between crimping jaws 60, thus replacing suture fastener 28.

Pusher element 54 can thereafter retract into shaft 14 and engage the next suture fastener of reserve suture fasteners 52 through rear openings 34 of the suture fastener, and stack gate 56 can remain in its original position to prevent the remainder of reserve suture fasteners 52 from contacting fastener delivery end 16 until second control mechanism is subsequently activated. Reserve suture fasteners 52 can include any number of suture fasteners which fit upon the length of rail 50 within shaft 14.

The configuration of rail 14 and fastener delivery end 16 provides several advantages. As described, crimping jaws 60 allow for deforming suture fastener 16 into a bent shape. The bent shape is particularly advantageous as it prevents an end of suture fastener 28 that would otherwise be upright from damaging any tissue within the body that comes into contact with suture fastener 28 once deployed. Additionally, suture cutting blade 58 provides the advantage of trimming excess ends of the suture near the crimping site, thereby excising a majority of the excess suture ends. As described above, the crimping of suture fastener 28, the bending of suture fastener 28, and the cutting of excess suture ends all occur in response to activation of the first control mechanism. Thus, suture fastener delivery device 10 provides the advantage of performing multiple functions of crimping, bending, and cutting, in response to a single control mechanism.

In addition, the mechanism of reserve suture fasteners 52 is particularly advantageous. Because shaft 14 houses a plurality of reserve suture fasteners 52, and because suture fastener 28 can be replaced via the second control mechanism upon handle 12 once suture fastener 28 is deployed, suture fastener delivery device 10 allows for deploying multiple suture fasteners without having to remove suture fastener delivery device 10 from the surgical site. Rather, suture fastener delivery device 10 can remain within the surgical site, deploying multiple suture fasteners as additional fasteners of reserve suture fasteners 52 are sequentially pushed to fastener delivery end 16 in response to activation of slider 20, and can thereafter be deployed.

Figure 7A:
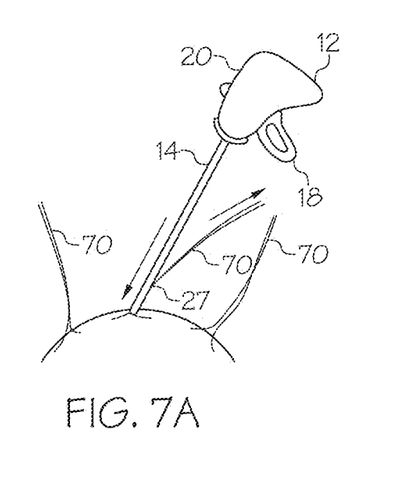
FIG. 7A is a diagram of the suture fastener and delivery device in a suture engagement position.
Figure 7B:
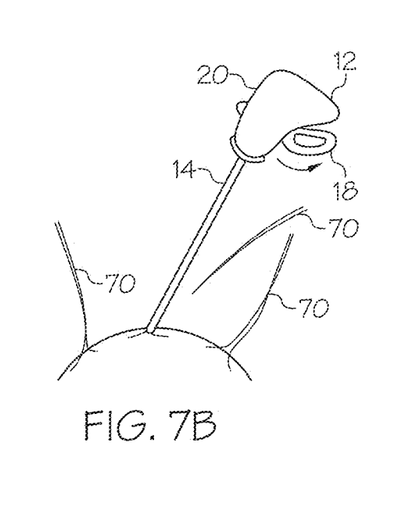
FIG. 7B is a diagram of the suture fastener and delivery device upon activation of a control element.
Figure 7C:
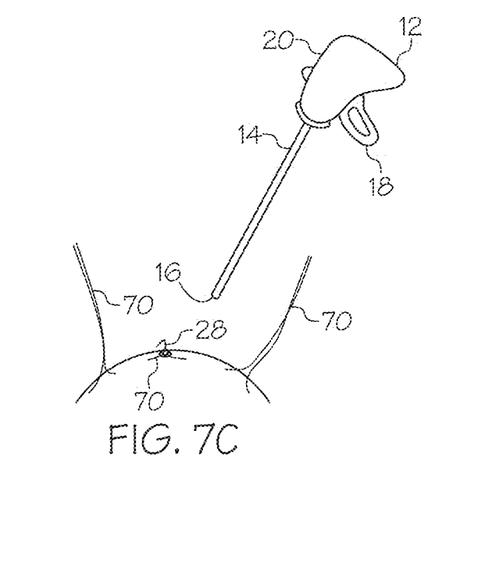
FIG. 7C is a diagram of the suture fastener and delivery device after deployment of the suture fastener and detachment of the suture fastener delivery device.

FIG. 7A is a diagram of suture fastener delivery device 10 in a suture engagement position. FIG. 7B is a diagram of the suture fastener delivery device 10 upon activation of the first control mechanism. FIG. 7C is a diagram of the suture fastener delivery device 10 after deployment of suture fastener 28 and detachment of suture fastener delivery device 10. FIGS. 7A-7C will be discussed concurrently.

As described above, a portion of an implanted suture 70 can be received within suture fastener 28 via a side cavity (i.e., slot 33) of suture fastener 28, and at least a portion of the suture ends of suture 70 can extend through side suture slot 27. FIG. 7A depicts suture fastener delivery device 10 in a suture engagement position wherein suture 70 is contained within body 32 of suture fastener 28, and at least a portion of the suture ends extend through side suture slot 27.

FIG. 7B depicts the response of suture fastener delivery device 10 upon activation of the first control mechanism. As depicted, suture 70 is cut via suture cutting blade 58, and the excess suture ends are therefore detached from suture 70. The suture ends can thereafter be easily removed, as the suture ends extend through side suture slot 27. Further, within suture fastener delivery device 10 at fastener delivery end 16, suture fastener 28 is deformed by crimping jaws 60. As described, crimping jaws 60 are configured to deform suture fastener 28 into a bent configuration.

FIG. 7C depicts suture fastener 28 after deployment. After suture fastener 28 is deployed, suture fastener delivery device is moved away from suture 70 while suture fastener 28 remains fixed to suture 70, thereby securing suture 70. As described, suture fastener 28 is in a deformed and bent state due to the closure of crimping jaws 60 in response to the activation of the first control mechanism. As depicted, suture fastener 28 is therefore bent, which minimizes the danger to surrounding tissue. Further, suture fastener 28 is oriented such that collar 31 rests upon the tissue at the suture site. The shape of collar 31 can remain substantially the same even after deformation occurs via crimping jaws 60. As described, crimping jaws 60 are positioned about outer surface 35, and hence body 32 undergoes deformation while collar 31 retains its shape. Thus, collar 31 rests upon the tissue in its original shape such that a front surface of collar 31 is in contact with the tissue.

After suture fastener 28 is deployed, the second control mechanism (e.g. slider 20) can be activated by the operator. Upon activation of the second control mechanism, the most distal suture of reserve suture fasteners 52 is pushed by pusher element 54 over stack gate 56 such that the most distal suture of reserve suture fasteners is in contact with fastener delivery end 16, and ready to be affixed to an additional suture.

Figure 8A:
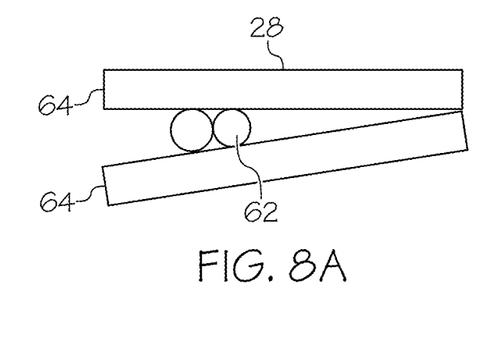
FIG. 8A depicts an alternative embodiment of the suture fastener configuration.
Figure 8B:
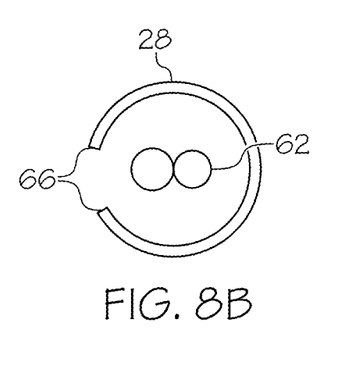
FIG. 8B depicts an additional alternative embodiment of the suture fastener configuration.

FIGS. 8A and 8B depict alternative embodiments of the configuration of suture fastener 28. FIG. 8A depicts one configuration wherein suture fastener 28 includes elongated elements 64 with sutures 62 resting in between the elongated elements 64. In such an embodiment, suture fastener 28 can be deformed via crimping jaw 60, thereby securing sutures 62. In another embodiment, a locking mechanism can exist to lock the unattached ends of elongated elements 64 after receiving sutures 62. FIG. 8B depicts another configuration wherein suture fastener 28 includes open loop element 66 with sutures 62 resting within open loop element 66. In such an embodiment, suture fastener 28 can be deformed via crimping jaw (i.e., crimping jaw 60), thereby securing sutures 62. In another embodiment, a locking mechanism can exist to lock the unattached ends of open loop element 66 after receiving sutures 62. In the embodiment of FIG. 8B, suture fastener 28 can be made from, for example, nitinol or any other material with shape memory and/or super-elastic properties.

The techniques of this disclosure relate to a suture fastener delivery device and corresponding suture fastener. The suture fastener delivery device includes a controller, a shaft, and a fastener delivery mechanism. The suture fastener delivery device captures a suture within a side opening of the suture fastener while allowing the suture ends to exit through a curved cavity in the side of the shaft. The suture fastener delivery device, in response to a single input of a control device, deforms the suture fastener to secure the suture, bends the suture fastener in a predetermined direction, and cuts the excess ends of the suture. The suture fastener delivery device then reloads the suture fastener from reserve suture fasteners which are stored in the body of the shaft. Thus, an operator of the suture fastener delivery device is able to deploy many fasteners in succession without removing the device from the surgical environment.

As used herein, the terms "substantially" or "generally" refer to the complete or nearly complete extent or degree of an action, characteristic, property, state, structure, item, or result. For example, an object that is "substantially" or "generally" enclosed would mean that the object is either completely enclosed or nearly completely enclosed. The exact allowable degree of deviation from absolute completeness may in some cases depend on the specific context. However, generally speaking, the nearness of completion will be so as to have generally the same overall result as if absolute and total completion were obtained. The use of "substantially" or "generally" is equally applicable when used in a negative connotation to refer to the complete or near complete lack of an action, characteristic, property, state, structure, item, or result. For example, an element, combination, embodiment, or composition that is "substantially free of" or "generally free of" an ingredient or element may still actually contain such item as long as there is generally no measurable effect thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or"

refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description should be read to include one or at least one and the singular also includes the plural unless it is obvious that it is meant otherwise.

Still further, the figures depict preferred embodiments for purposes of illustration only. One skilled in the art will readily recognize from the discussion herein that alternative embodiments of the structures and methods illustrated herein may be employed without departing from the principles described herein.

While particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

While the systems and methods described herein have been described in reference to some exemplary embodiments, these embodiments are not limiting and are not necessarily exclusive of each other, and it is contemplated that particular features of various embodiments may be omitted or combined for use with features of other embodiments while remaining within the scope of the invention.

The invention claimed is:

1. A suture fastener delivery device, comprising:
    a controller positioned on a proximal end of the suture fastener delivery device, the controller comprising at least one control element;
    a fastener delivery end positioned on a distal end of the suture fastener delivery device, the fastener delivery end comprising:
        a suture fastener configured to be deployed to secure a suture;
        crimping jaws positioned about an outer surface of the suture fastener;
    a shaft extending between the controller and the fastener delivery end from the proximal end to the distal end of the suture fastener delivery device, the shaft comprising:
        a rail extending along an interior length of the shaft;
        a plurality of reserve suture fasteners mounted along the rail;
        a side suture slot positioned about a side of the shaft, the side suture slot configured to allow the suture to exit the suture fastener delivery device; and
        a suture cutting blade, the suture cutting blade positioned adjacent to the rail within the shaft.

2. The device of claim 1, wherein the suture fastener comprises a side opening and wherein the suture fastener is configured to receive the suture though the side opening.

3. The device of claim 1, wherein the fastener delivery end further comprises a suture trap, configured to receive the suture and pass the suture into the suture fastener.

4. The device of claim 1, wherein a suture trap comprises a one-way channel allowing sutures to enter the suture trap from a top side of the one-way channel.

5. The device of claim 1, wherein the at least one control element comprises a trigger and a slider.

6. The device of claim 1, wherein the crimping jaws are configured to crimp the suture fastener around the suture in response to activation of the at least one control element, thereby securing the suture.

7. The device of claim 1, wherein the suture cutting blade is configured to move in a direction substantially parallel to the rail to cut a trailing end of the suture in response to activation of the at least one control element.

8. The device of claim 1, wherein the suture fastener is bent in the first direction in response to activation of the at least one control element.

9. The device of claim 1, wherein the plurality of reserve suture fasteners are positioned as a spring-loaded stack.

10. The device of claim 9, wherein the shaft further comprises a stack gate configured to halt the spring-loaded stack of the reserve suture fasteners from contacting the fastener delivery end.

11. The device of claim 10, wherein the shaft further comprises a pusher element, and wherein in response to activation of the at least one control element, the pusher element pushes a most distal suture fastener of the reserve suture fasteners over the stack gate and into contact with the fastener delivery end.

12. The device of claim 11, wherein, the pusher element comprises two tines.

13. The device of claim 1, wherein the suture fastener has a C-shaped cross-section.

14. The device of claim 1, wherein the suture fastener is integrally formed as a singular piece.

15. The device of claim 1, wherein the suture fastener comprises a collar on the suture fastener, the collar configured to rest upon tissue when the suture fastener is deployed.

16. The device of claim 1, wherein the side suture slot is a curved three-dimensional feature allowing one directional passage of sutures.

17. The device of claim 1, wherein the suture fastener comprises two elongated elements and a locking mechanism.

18. The device of claim 1, wherein the suture fastener comprises an open loop element and a locking mechanism, the open loop element being made of nitinol.

* * * * *